United States Patent [19]
Meriläinen et al.

[11] Patent Number: 5,542,285
[45] Date of Patent: Aug. 6, 1996

[54] METHOD AND APPARATUS FOR TRANSIENT TEMPERATURE COMPENSATION IN GAS ANALYZER EQUIPMENT

[75] Inventors: Timo Meriläinen; Börje Rantala, both of Helsinki; Kurt Weckström, Espoo, all of Finland

[73] Assignee: Instrumentarium Corp., Finland

[21] Appl. No.: 332,692

[22] Filed: Nov. 1, 1994

[30] Foreign Application Priority Data

Nov. 3, 1993 [FI] Finland ................... 934871

[51] Int. Cl.$^6$ ............................. G01N 21/17; G01J 5/12
[52] U.S. Cl. ............................. 73/23.21; 250/343
[58] Field of Search ................. 73/23.21; 250/343–346; 374/129, 181

[56] References Cited

U.S. PATENT DOCUMENTS

| | | | |
|---|---|---|---|
| 3,745,349 | 7/1973 | Liston | 250/565 |
| 4,423,739 | 1/1984 | Passaro et al. | 128/719 |
| 4,772,790 | 9/1988 | Aldridge | 250/343 |
| 4,950,900 | 8/1990 | Takeuchi et al. | 250/346 |
| 5,056,929 | 10/1991 | Watanabe et al. | 374/181 |
| 5,150,969 | 9/1992 | Goldberg et al. | 374/128 |
| 5,223,716 | 6/1993 | Rossiter | 250/343 |

FOREIGN PATENT DOCUMENTS

| | | |
|---|---|---|
| 222993 | 5/1987 | European Pat. Off. . |
| 91/03204 | 3/1991 | WIPO . |
| 91/05240 | 4/1991 | WIPO . |
| 91/18279 | 11/1991 | WIPO . |
| 93/09413 | 5/1993 | WIPO . |

OTHER PUBLICATIONS

Johnston, "Gas Monitors Employing Infrared LED's", Meas. Science & Technology, Mar.(1992) pp. 191–195, UK.

*Primary Examiner*—Michael J. Brock
*Attorney, Agent, or Firm*—Andrus, Sceales, Starke & Sawall

[57] ABSTRACT

The invention relates to a method and apparatus for temperature compensation in gas analyzer equipment for transient error caused by temperature change. According to the method, a radiation source (1) is used for transmitting electromagnetic radiation through a gas mixture to be analyzed, the intensity of radiation transmitted through the gas mixture being analyzed is detected by means of a thermal detector (4) comprising a radiation detecting sensor element (16) and a reference sensor element (17) for generating an output signal proportional to the concentration of gas being analyzed, the temperature of said thermal detector (4) is measured either directly or indirectly, the measured detector temperature values are recorded as a function of time, and the output signal of the thermal detector (4) is temperature compensated by a correction term dependent on the temperature rate of change (DT) of the thermal detector. According to the invention, the uncorrected output signal $V_{mass}$ of the thermal detector (4) is temperature compensated by adding a correction term $V_{comp}$ dependent on the temperature rate of change (DT) of the thermal detector to said output signal.

30 Claims, 6 Drawing Sheets

METHOD AND APPARATUS FOR TRANSIENT TEMPERATURE COMPENSATION IN GAS ANALYZER EQUIPMENT

BACKGROUND OF THE INVENTION

The invention is related to a method for temperature compensation of gas analyzer equipment for transient error caused by temperature changes.

The invention also concerns an apparatus with temperature compensation of transient error in gas analyzer equipment caused by temperature changes.

The invention further concerns a method and an apparatus for improving the measurement accuracy of a gas analyzer based on thermal detection of infrared radiation, in particular under changes in the operating temperature of the analyzer.

The invention is particularly suited to applications in which the infrared radiation intensity is determined by a direct or indirect measurement of the temperature difference produced between the sensor element detecting the impinging radiation and a reference element. Such a detector has the inherent shortcoming that a change in the ambient temperature disturbs the internal thermal balance of the detector, and resultingly, the output signal will contain a transient error which degrades the accuracy of the gas analyzer during the temperature change. The thermal detector used in the measurement may advantageously be a thermopile detector.

The method according to the invention is suited for use in gas analyzers designed to perform either the identification or measurement of concentration, or alternatively, both the identification and measurement of concentration, of at least one component of a gas sample. Such a gas analyzer can be used for, e.g., monitoring the composition of the airway gases of a patient anesthetized for the duration of an operation, whereby the gases to be determined can include at least carbon dioxide ($CO_2$), nitrous oxide ($N_2O$) as well as at least one anesthetic agent.

The thermopile detector measures the infrared absorption of gas introduced to a sampling chamber, after which the concentration of the desired gas component is determined from the measured absorption.

Thermopile detectors are used in gas analyzers among other things owing to their capability of DC measurement which facilitates a cost-effective construction of the measurement system. The wavelength range of thermopile detectors is suitable for infrared measurements, since the absorption bands centering about the 10 µm wavelength fall within the spectral sensitivity wavelength range of the detector. Moreover, thermopile detectors have a high sensitivity and good linearity.

A characteristic of the thermopile detector is that with a change of its external housing temperature after, e.g., a cold start-up of the analyzer or due to an ambient temperature change, the detector output will contain a transient error which degrades measurement accuracy over the duration of the transient state.

With reference to U.S. Pat. No. 4,423,739 (Passaro), the gas analyzer output signal can be compensated for thermal drift by means of a chopper which intermittently blocks the radiation path from the lamp to the detector, thus permitting measurement of detector output signal offset which is then subtracted from the detector output signal when the radiation is again permitted to impinge on the detector. The moving mechanical components of..the chopper make the analyzer not only large and costly, but lower its operational reliability.

With reference to U.S. Pat. No. 3,745,349 (Liston), a gas analyzer can also be stabilized by way of modulating the radiant output power of its infrared source. However, such modulation is possible only at a relatively low frequency, which thus limits the response speed of the gas analyzer.

As is disclosed in the PCT publication WO91/18279 (Apperson), the error related to the temperature change can be avoided by thermostatting the operating temperature of the infrared detectors. However, as the thermopile is substantially disturbed even by the slowest changes in its operating temperature, the temperature control system must have a slow response with low drift. Such a slow response results in retarded start-up of the analyzer. Designing the temperature control system for low drift makes is costly. Heating/cooling arrangements in turn increase the power consumption and size of the analyzer.

With reference to U.S. Pat. No. 4,772,790 (Aldridge), a gas analyzer based on a thermopile detector is disclosed in which a quadruple detector array encapsulated in a single package is subjected to infrared radiation so that the radiation components passed through the sample gas cell and attenuated by the gases under measurement are arranged to impinge on three measurement sensor elements, while such a wavelength of the radiation passed through the sample gas cell that is free from absorptive attenuation by the gases under measurement is arranged to impinge on one sensor element acting as the reference element. Then, the thermal drift caused temperature change can be compensated by subtracting the output signal of the reference element from the output signals of the measurement sensor elements. The system is hampered by the need for a band pass filter centered at the reference wavelength which contributes to the higher cost of the analyzer. Moreover, the requirements set to the measurement electronics are tightened substantially, because the output voltage of each sensor element in the quadruple detector structure is maximally one-fourth of the output voltage of an equivalent-size single sensor element package.

Replacing the filter centered at the reference wavelength, one of the sensor elements of the thermopile package can be covered with a foil opaque to infrared radiation such as a metal foil. Then, the temperature compensation can be made by subtracting the output voltage of the covered sensor element from the output voltage of the measurement sensor element. This approach is hampered by the need for the extra sensor and that the operating temperature differences of the sensor elements with their different temperature drift characteristics cause incorrect compensation.

With reference to WO patent publication 91/03204 (Yelderman), the output signal error caused by the temperature drift of the thermopile detector is compensated by performing the radiation absorption measurement of the gas of interest by means of two thermopile detectors encapsulated in a single package, whereby in front of one of the sensor elements is placed a filter with an optical attenuation of, e.g., 50% to the radiation wavelength being measured. Then, the temperature change affects both detectors in the same manner, whereby the effect of the temperature-dependent transient error is compensated when the difference of the detector output voltages is formed. Owing to the radiation-attenuating filter placed in front of one sensor element, the differential output voltage of the sensor elements is still proportional to the incident radiation intensity. The method is hampered by the need for a dual detector and an auxiliary filter having a specified attenuation characteristic for the incident radiation. Due to the use of a dual detector and formation of a difference of the detector output voltages, the output voltage of such a compensated detector is maximally one-fourth of the output voltage of an equivalent-size single sensor element package.

Sensing of the internal temperature of thermopile detectors used in gas analyzers has been employed in some applications. However, such simple temperature information has not proven sufficient for the compensation of thermal drift under a transient situation or change in ambient temperature.

SUMMARY OF THE PRESENT INVENTION

It is an object of the present invention to overcome the shortcomings of the above-described prior-art techniques and to achieve an entirely novel type of method and apparatus for the compensation of thermal drift in a gas analyzer.

The invention is based on compensating the thermal drift of a gas analyzer by means of measuring the temperature of the thermal infrared detector, or the temperature of the detector package advantageously having the same temperature as the detector or, advantageously, the temperature of the analyzer body piece having the same temperature as the detector package, and then adding a correction signal dependent on the temperature rate of change to the detector output signal.

The gas analyzer used in conjunction with the invention may comprise a number of filters and detectors, whereby the concentration of a multiplicity of gases of interest can be determined on-line from the sample mixture of gases. All the detectors may be mounted on a single body piece thus facilitating the temperature measurement of all detector packages by means of a single temperature sensor employed to measure the temperature of said body piece.

The invention offers significant benefits.

By virtue of the method according to the invention, the gas analyzer can be implemented without resorting to an optical chopper, modulation of the radiation source or other thermal detectors except those employed in the optical absorption measurement of the gas of interest. Further, the infrared detectors of the gas analyzer require no arrangements of constant temperature control.

BRIEF DESCRIPTION OF THE DRAWING

In the following, the invention will be examined in more detail by means of exemplifying embodiments with reference to the attached drawings, in which.

DETAILED DESCRIPTION OF THE PREFERRED EMBODIMENTS

Figure 1:
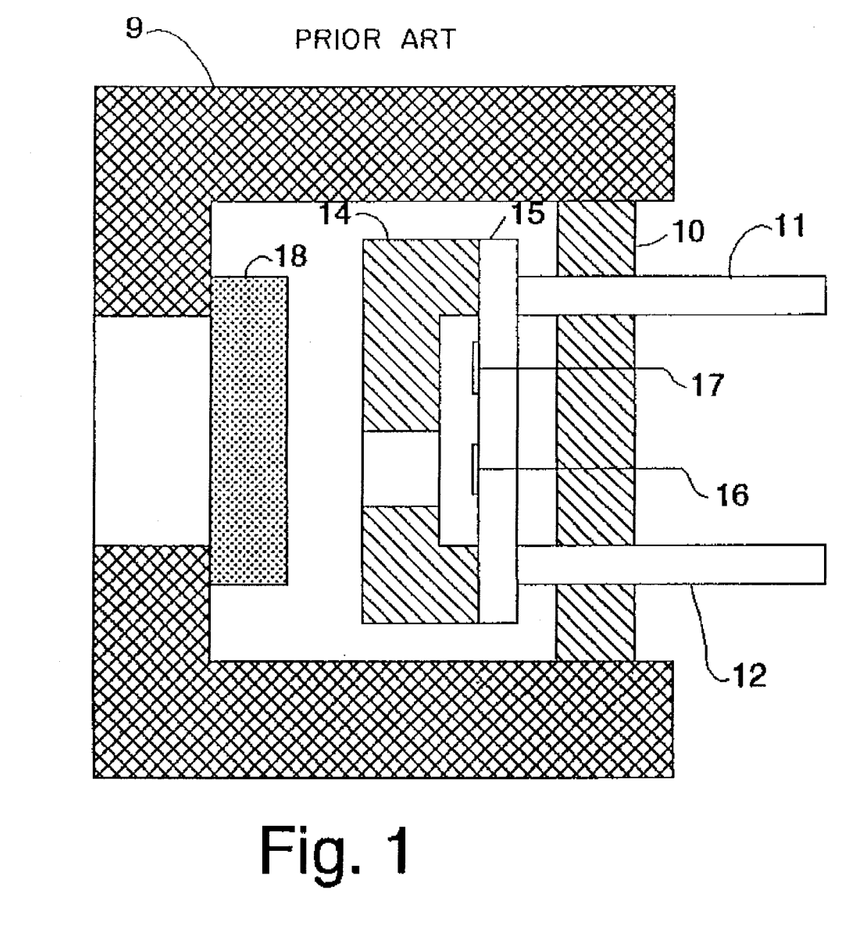
FIG. 1 is a longitudinally sectional side view of the structure of a conventional thermopile.
Figure 2:
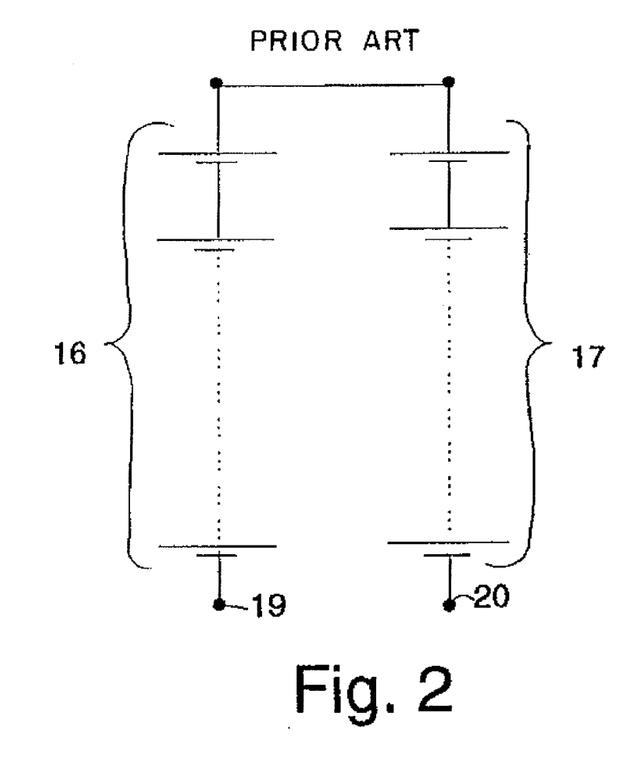
FIG. 2 is the electrical equivalent circuit of the thermopile illustrated in FIG. 1.

With reference to FIGS. 1 and 2, a thermopile detector package comprises a hermetic case 9, a seal plug 10, conductors 11 and 12, a mask cap 14, a foil 15, a radiation detecting sensor element 16 and a reference sensor element 17 and a window 18. The thermopile sensor elements 16 and 17 comprise one or a greater number of series-connected junctions of two different materials, each junction being denominated a thermocouple, whereby a temperature-dependent voltage is generated over such a junction by the known Seebeck effect. The output voltage of a thermopile is the sum of the individual junction voltages of the series-connected thermocouples forming the thermopile. The thermopiles of the detector are fabricated on a thin-film substrate 15 and are connected opposedly in series as illustrated in FIG. 2 so that the output voltage of the thermopile detector available over terminals 19 and 20 is zero when the thermopiles are at the same temperature. The output voltage is taken to conductors 11 and 12 which are passed out from the detector package via a seal plug 10. The thermopiles 16 and 17 are placed on the thin-film substrate 15 so that the radiation impinging onto the detector through a window made to the mask cap 14 can heat only one of the sensor elements (e.g., element 16), while the other sensor element (e.g., element 17) remains at the same temperature with the mask cap. Hence, the output voltage of the detecting sensor element 16 heated by the impinging radiation increases, whereas the output voltage of the reference sensor element 17 remains constant. Consequently, the output voltage of the thermopile detector increases with increasing intensity of the radiation impinging onto the detector.

Such a thermopile detector 4 operates perfectly only when its internal temperature gradient remains unchanged. Typically, the thermopile 16 performing as the active sensor element is effectively thermally isolated from its substrate to increase the sensitivity and response speed of the detector. By contrast, the reference sensor element 17 is provided with a good thermal contact with its substrate. Thus, when the temperature of the case 9 of the detector 4 changes, the internal temperature gradient of the detector 4 is disturbed, and an error signal is summed to the detector output signal principally caused by the fact that a temperature gradient is established between the thermopiles 16 and 17, whereby the disturbing temperature gradient is larger the faster the temperature rate of change in the case 9 of the thermopile detector 4. Such a disturbance may be caused by, e.g., radiation leakage through the case 9 and the window 18 onto the radiation detecting sensor element 16.

Figure 3:
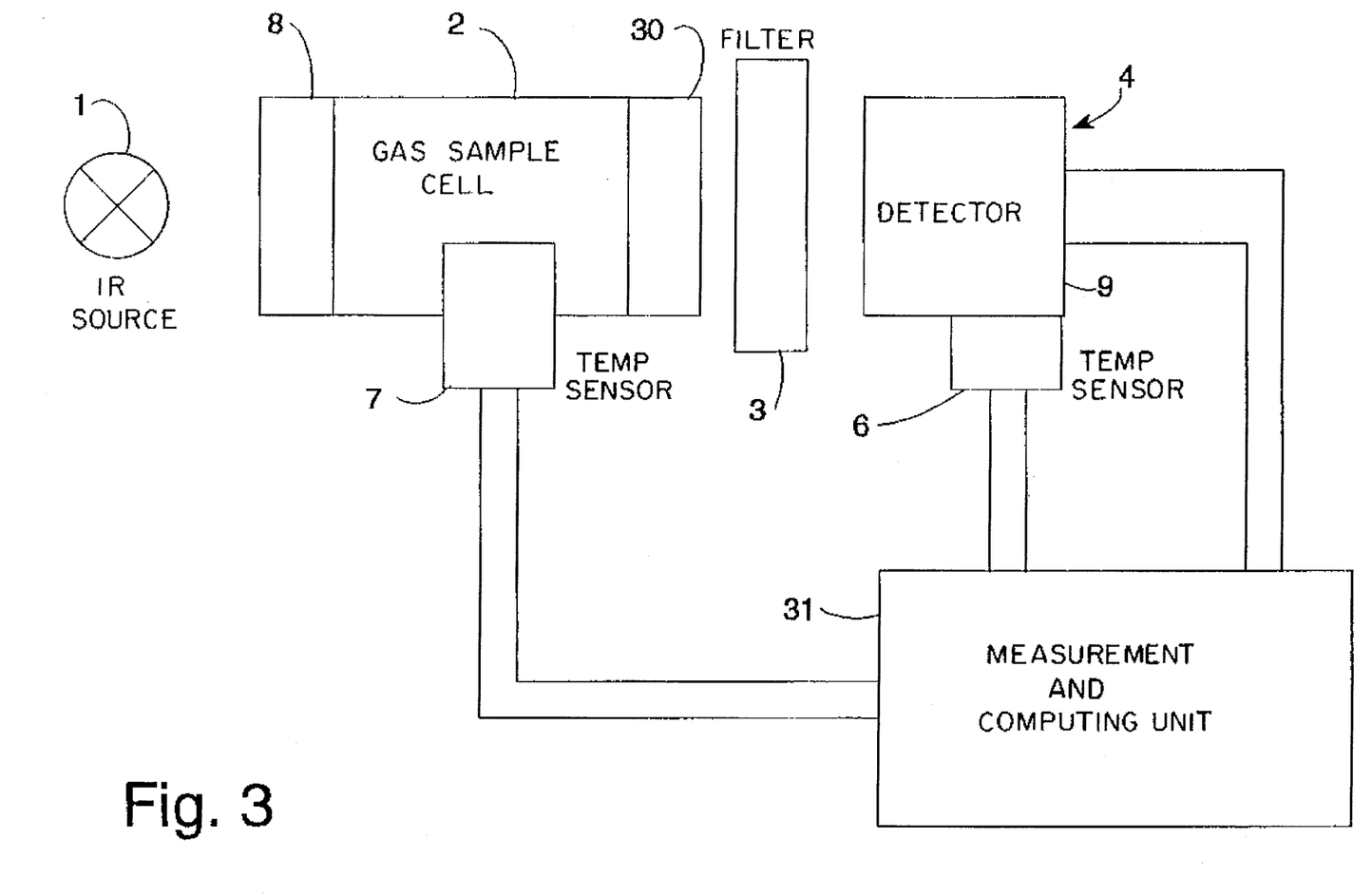
FIG. 3 is a diagrammatic side view of an embodiment of a gas analyzer according to the invention.

With reference to FIG. 3, the gas analyzer comprises an infrared radiation source 1 which may be a resistance wire such as Type A-1 by Kanthal AB, for instance, heated by electric current. Close to the infrared source 1 is placed a sample gas cell 2 having windows 8 and 30 at its opposite sides made from infrared radiation transmitting material such as, e.g., calcium fluoride.

Along the path of the infrared beam, next to the sample gas cell 2 is placed an optical bandpass filter 3 which is made transmissive only at the wavelength of the absorption band of the gas of interest.

Further along the path of the infrared beam, after the sample gas cell 2, and advantageously also after the optical bandpass filter 3 is placed a thermopile detector 4 such as type DK2M by Dexter Research Center, Inc., for instance. The temperature of the case 9 of the detector 4 is measured by means of a temperature sensor 6. The temperature of the case 9 of the detector 4 is typically the same as the temperature of the reference sensor element 17 shown in FIG. 1. The temperature sensor 7 which measures the temperature of the sample gas mixture is placed in conjunction with the sample gas cell 2. A measurement and computing unit 31 processes the output signals of sensor elements 6, 7 and 4, and provides the control thereof.

The radiation emitted by the infrared source 1 is taken through a window 8 to the sample gas cell 2 containing the gas mixture to be analyzed. The gas to be analyzed for its concentration absorbs radiation at a wavelength band which is the same as the spectral passband range of an optical filter 3. Alternatively, the filter 3 may advantageously be an optical interference filter such as manufactured by Optical Coating Laboratories, Inc. The radiant energy passing from the chamber 2 through a window 30 and the filter 3 to the detector 4 is lower the higher the concentration of the gas of interest in the sample gas mixture. Determination of the gas concentration also requires measurement of the sample gas mixture temperature which is accomplished by means of a temperature sensor 7.

Figure 4:
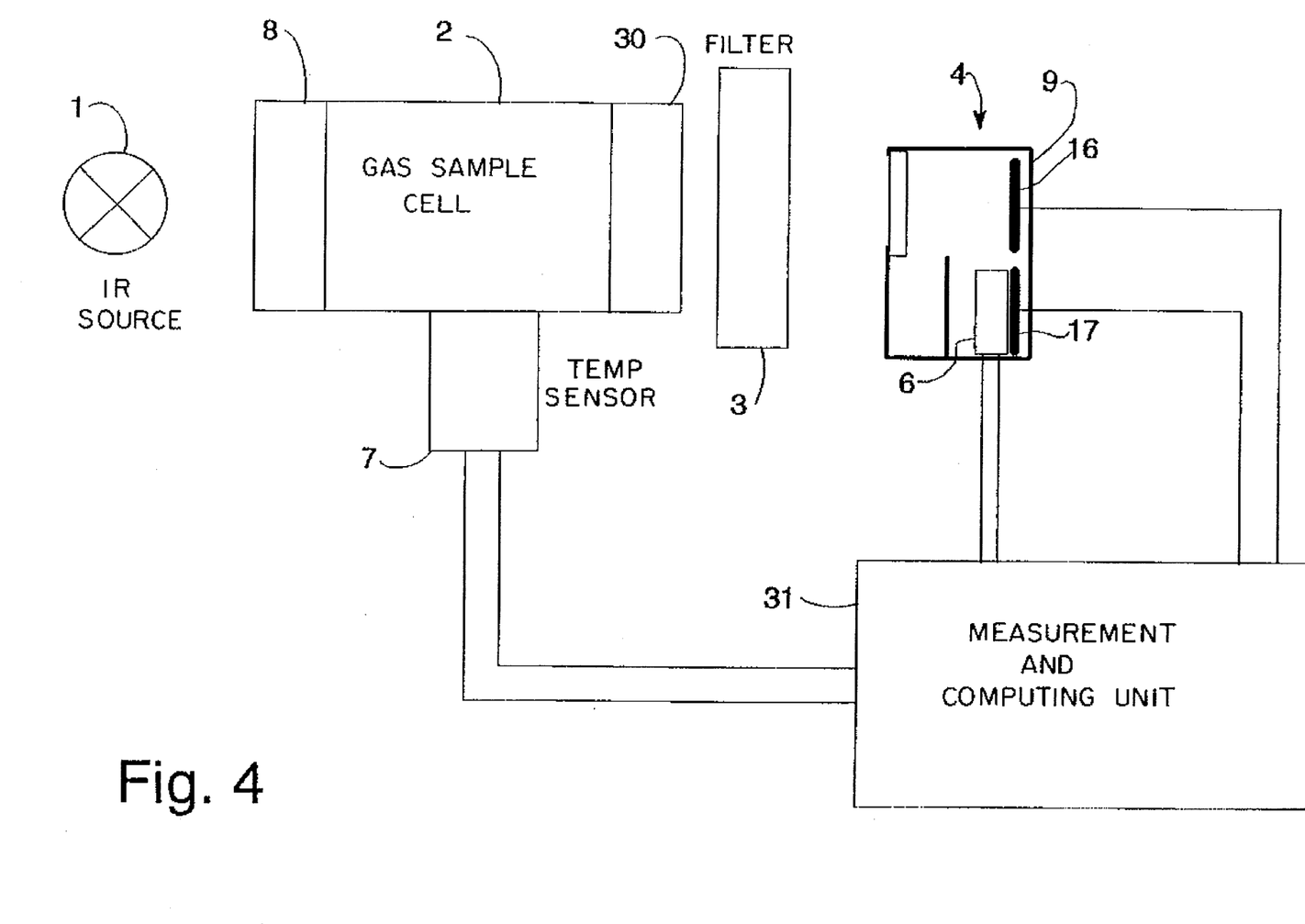
FIG. 4 is a diagrammatic side view of another embodiment of a gas analyzer according to the invention.

With reference to FIG. 4, an alternative embodiment is shown in which the temperature of the reference sensor element 17 of the detector 4 is sensed by a temperature sensor 6 placed inside the package of the detector 4.

Figure 5:
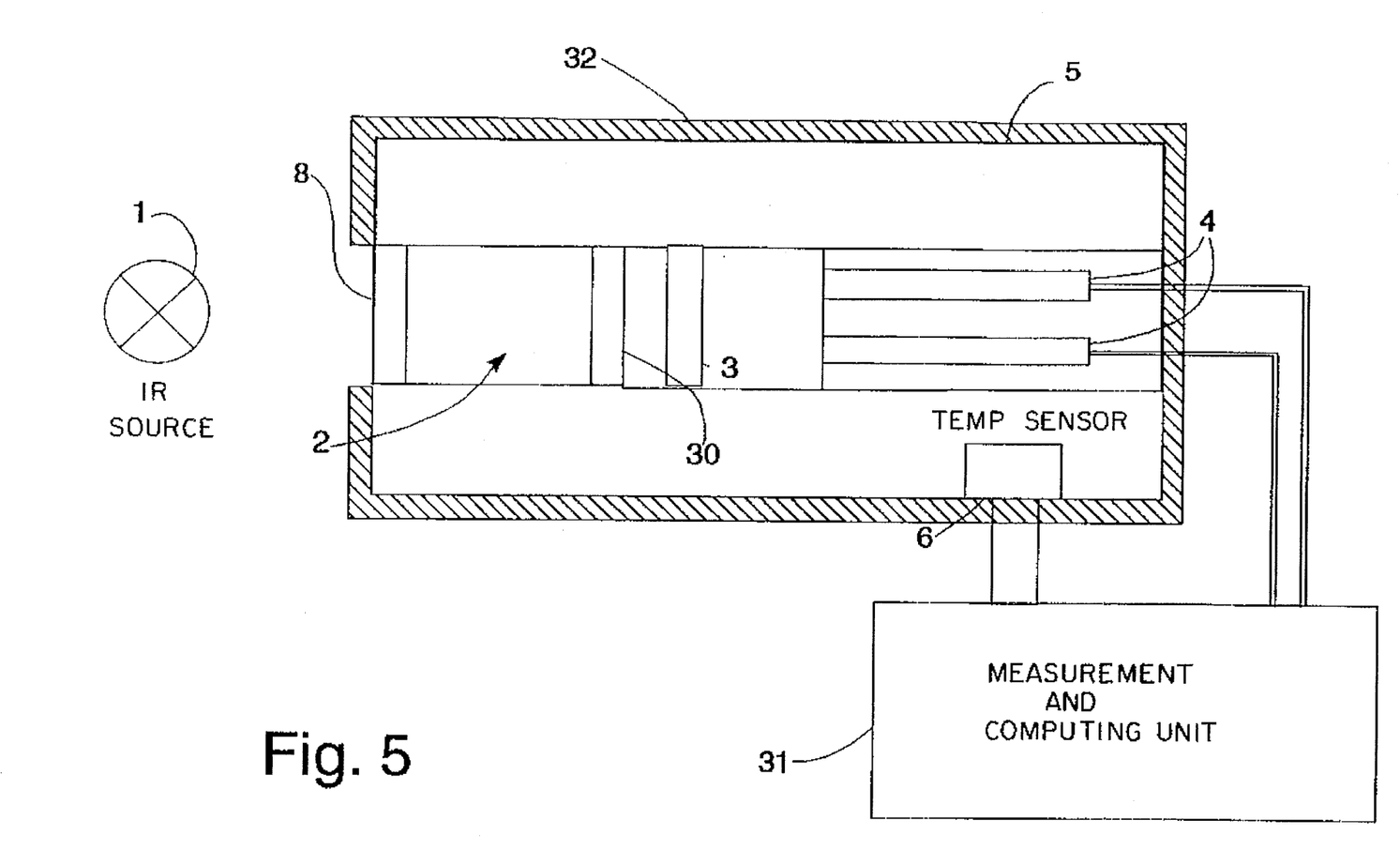
FIG. 5 is a diagrammatic side view of a third embodiment of a gas analyzer according to the invention.

With reference to FIG. 5, a further alternative embodiment is shown in which the sample gas cell 2 is placed inside the body piece 5 and thus maintained at the same temperature with the body piece. By virtue of such a construction, a single temperature sensor 6 is sufficient for measuring the temperature of both the detector body piece and the sample gas mixture.

The placement of the temperature sensor is desirably characterized by "thermal intimacy", that is, the temperature of the temperature sensor 6 must change as simultaneously with and at the same temperature rate of change as the temperature of the reference sensor element 17 of the detector 4 varies.

Such a "thermal intimacy" can be accomplished either by means of the direct measurement illustrated in FIG. 4, or alternatively, by measuring the detector case temperature as illustrated in FIG. 3. Direct temperature measurement of the reference sensor element 17 requires, however, the use of a special construction detector with an integral temperature sensor. The heat dissipation of such an integral temperature sensor may cause an error to the measurement accuracy of the thermal detector by introducing a temperature-gradient disturbing heat source to the interior of the detector. The case temperature measurement of the detector presumes a small temperature sensor with a fast response having a construction which is not sensitive to disturbance by external sources of heat. Also this arrangement is subject to error from the heat dissipated by the temperature sensor. If a multiplicity of detectors are used in the gas analyzer, the above-described detector constructions must also be provided with a plurality of temperature sensors. In such constructions the temperature rate of change may be so fast that the compensation method according to the invention fails to perform with sufficient accuracy.

It is an object of the present invention to achieve a simple apparatus in which the temperature rate of change in the infrared detector, and resultingly, the transient thermal drift of the detector output signal remain so small as to yield a good measurement accuracy by virtue of the compensation method according to the invention. In the construction according to the invention the temperature measurement of one or a greater number of infrared detectors can be accomplished by means of a single temperature sensor whose heat dissipation has an insignificant effect on the output signal of the detectors. The apparatus according to the invention is shown in FIG. 5. Therein, one or a greater number of infrared detectors 4 are mounted in a body piece 5 of high thermal conductivity also incorporating a temperature sensor 6. The body piece is enclosed in thermal insulation 32.

Owing to the high thermal conductivity of the body piece 5 and its enclosing thermal insulation 32, its temperature can change only slowly even if the ambient temperature about the thermal insulation 32 would vary extremely rapidly due to, e.g., changes in the ambient temperature or in conjunction with the analyzer start-up. Since the temperature variations of the body piece 5 are slow and the body piece 5 is made from a material of high thermal conductivity, it stays very accurately at an uniform temperature. Resultingly, the temperature of the temperature sensor 6 stays very accurately the same changing simultaneously with and at the same temperature rate of change as the temperature of the reference sensor element 17 of the one or a greater number of detectors 4 mounted in the body piece 5 varies. The body piece 5 can be, e.g., an aluminum block with a weight of 170 g enclosed in thermal insulation of, e.g., at least 2 mm thick expanded polyethylene plastic sheet such as the Plastazote product with a thermal conductivity of 0.046 W/m° K. manufactured by Fagerdala Tuotanto Oy. The thermal time constant of such a thermally insulated body piece 5 is greater than 15 min, advantageously approx. 20 min, and for an abrupt change of ambient temperature by 10° K., the temperature rate of change of the body piece 5 remains smaller than 0.5° K./m.

Owing to the good thermal conductivity of the body piece 5, it has the same temperature all over the piece. Resultingly, the temperature sensor 6 is at the same temperature as the one or a greater number of infrared detectors 4 mounted to the body piece 5. As the temperature of the body piece 5 changes slowly, also the precondition is fulfilled that the temperature variation of the temperature sensor 6 occurs simultaneously with and at the same temperature rate of change as the temperature of the infrared detectors varies. Hence, the construction according to the invention implements all the requirements set for the "thermal intimacy" between the temperature sensor and the infrared detectors using only a single temperature sensor.

Since the body piece has a high thermal capacity and possesses good thermal conductivity, the thermally-induced error in the detector output signal due to the heat dissipation of the temperature sensor remains smaller than in conventional constructions. The temperature measurement can be implemented by means of measuring the reference sensor element temperature as illustrated in FIG. 4, measuring the detector case temperature as in FIG. 3, or alternatively, using the body piece construction of high thermal conductivity as in FIG. 5.

Figure 6:
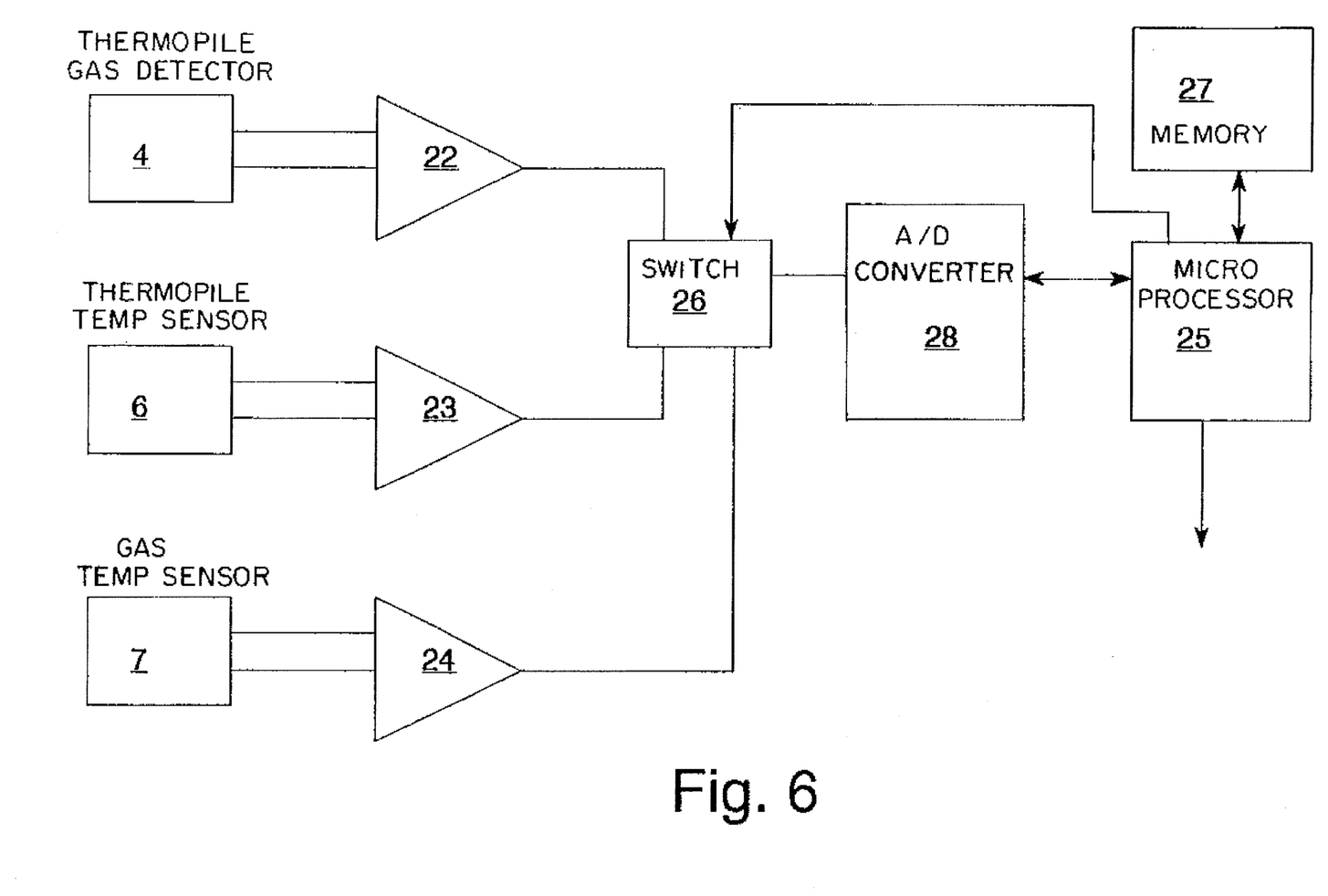
FIG. 6 is a block diagram of the measurement electronics employed in a gas analyzer according to the invention.
Figure 7:
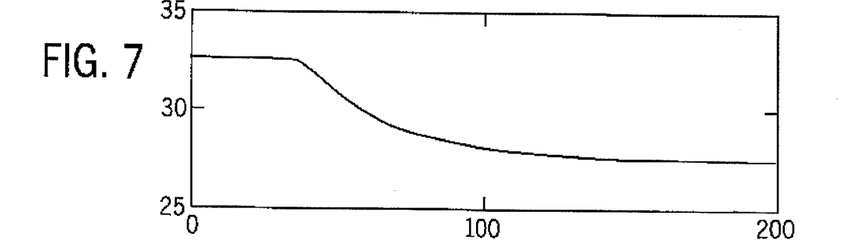
FIG. 7 is a representation of the temperature of the infrared detector reference element as a function of time when the ambient temperature of the analyzer is abruptly lowered by 5° C., the horizontal axis of the diagram is time in minutes while the vertical axis is temperature in degrees Celsius.
Figure 8:
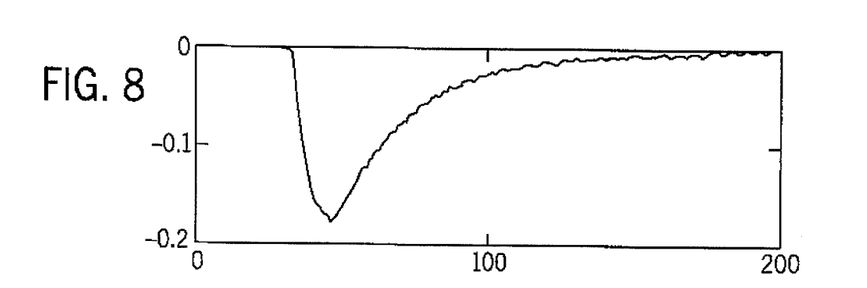
FIG. 8 is a representation of the temperature rate of change of the detector reference element as a function of time for the thermal response test illustrated in FIG. 7, the horizontal axis of the diagram is time in minutes while the vertical axis is temperature rate of change in degrees Celsius per minute.

With reference to FIG. 6, a measurement and computing unit 31 is shown capable of implementing the compensation method according to the invention. The unit comprises an output amplifier 22 for the signal of the thermopile detector 4, a measurement amplifier 23 for the sensor 6 of the detector head body piece temperature, a measurement amplifier 24 for the sensor 7 of the sample gas temperature, an analog-to-digital converter 28, a microprocessor 25, a switch 26 controlled by the microprocessor and a memory circuit 27. By controlling the switch, the microprocessor applies the output signal of the temperature measurement amplifier 23 to the analog-to-digital converter, then reads the digitized temperature value, and on the basis of the latest and previously measured temperature values and the interval between the measurements, computes the temperature rate of change, DT. In a similar fashion, the microcomputer also reads the amplified and digitized output voltages of the thermopile detectors and the sample gas mixture temperature. In the compensation method according to the invention, the microprocessor 25 then computes a corrected measurement voltage V which is formed as the sum of the output voltage $V_{meas}$ of the detector 4 and a compensation term $V_{comp}$:

$$V = V_{meas} + V_{comp}$$

$V_{comp}$ is dependent on the temperature rate of change DT and detector-specific compensation parameters which are recorded during the manufacture of the gas analyzer and stored in the memory circuit 27. Accordingly, these functions serve for compensation of the transient error in the detector output signal caused by temperature change. The temperature correction of the detector gain and other compensations such as those related to the zero signal level drift are accomplished by means of conventional techniques.

With reference to FIG. 2, the electrical equivalent circuit of a conventional detector unit is shown. The thermopiles 16 and 17 conventionally comprise an equal number of thermocouple junctions, whilst an unequal number can be employed as well. A plurality of separate detectors may be integrated in the same detector case.

The transparent optical window may be replaced by a suitable optical bandpass filter, or alternatively, the optical bandpass filter may be placed inside the detector case, between the optical window and the radiation detecting thermopile.

A multi-gas analyzer operates on several infrared wavelengths requiring typically one filter for each constituent of the gas mixture being analyzed. By mounting the filters on, e.g., rotating disk, only a single detector will suffice. If the analyzer performs measurements on a single wavelength alone, the optical bandpass filter may also be located between the source and the sample gas cell, or alternatively, it may replace one of the windows of the cell. In a multi-gas analyzer the filters may also be mounted between the rear window of the sample gas cell and the detectors, as a window of the sample gas cell, or alternatively, within the detector case between the detector case window and the radiation-responsive surface of the sensor element. The primary cause of the output signal error to be compensated for by means of the method according to the invention is the change in the detector case temperature. Hence, instead of measuring the detector case temperature directly, the temperature measurement can be performed at such a part of the gas analyzer where the temperature rate of change is equal to the rate of change of the detector case temperature. Accordingly, if one or a greater number of detectors are mounted on a body piece of high thermal conductivity such as an aluminium block, for instance, the temperature of all the detector cases remains with a sufficient tolerance the same as the body piece temperature which can be advantageously measured by means of a single, suitably located temperature sensor. Moreover, the temperature differences between the different parts of the common body piece of the detectors can be further equalized by isolating the body piece from external sources of heat with maximally effective thermal insulation. By making the temperature rate of change in the body piece slow, the magnitude of the thermal drift error can be limited thus improving the accuracy of the gas analyzer. This can be accomplished by, e.g., increasing the thermal mass of the body piece and isolating the body piece from external sources of heat. The body piece temperature can be determined by a single-point temperature measurement when the measurement point is appropriately selected. The compensation method according to the invention can be implemented using a plurality of different electronic circuitry by, e.g., replacing the microprocessor with entirely analog circuits.

According to the invention, the temperature at the location of the temperature sensor where the detector temperature rate of change is measured need not be the same as the detector case temperature. The essential requirement only is that the temperature rate of change at the location of the temperature sensor is substantially equal to the rate of change at the detector case.

Instead of the wideband source 1, an infrared source can be the one which emits at the absorption wavelength of the gas to be analyzed only. Then, the bandpass filters 3 can be omitted.

At a time instant t, the value of the compensation term $V_{comp}(t)$ may be written as a linear function of the temperature rate of change DT: $V_{comp}(t) = K_{comp} \cdot DT(t)$, where $K_{comp}$ = proportionality coefficient or a delayed function thereof: $V_{comp}(t) = K_{comp} \cdot DT(t-dt)$, where dt = delay, or a polynomial function of DT: $V_{comp}(t) = \Sigma K_{ncomp} \cdot DT(t)^n$, where n may be a nonintegral exponent, or a combination function of any above-given function.

Figure 9:
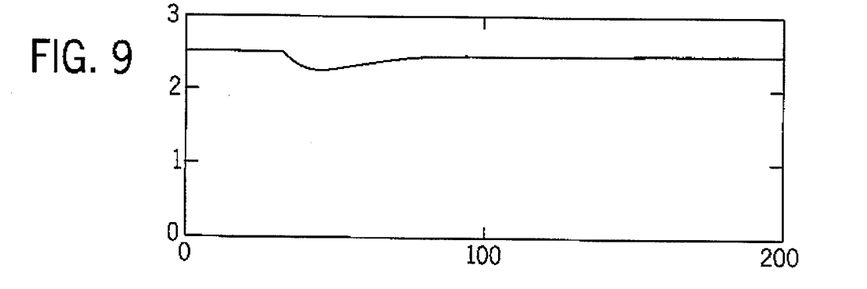
FIG. 9 is a representation of amplified detector output voltage with conventional thermal drift compensation during the thermal response test illustrated in FIG. 7, and as the sample gas cell is void of the gas of interest, the output voltage should remain unchanged during the test.

With reference to FIGS. 7–10, the essential signals of the compensation method according to the invention are plotted as functions of time. The horizontal axis in the diagrams is time in minutes. FIG. 9 exhibits clearly the nonlinear transient error caused by the temperature change of the reference sensor element of the detector illustrated in FIG. 7 on the sensor output signal $V_{meas}$, said output signal transient having a shape very close to that of the reference sensor temperature rate of change plotted in FIG. 8. Compensation is carried out by forming a correction voltage $V_{comp}(t)$ according to the following function:

$$V_{comp}(t) = -2.9 \cdot DT(t)^{0.95} - 0.15 \cdot DT(t-10)^{1.05}$$

Figure 10:
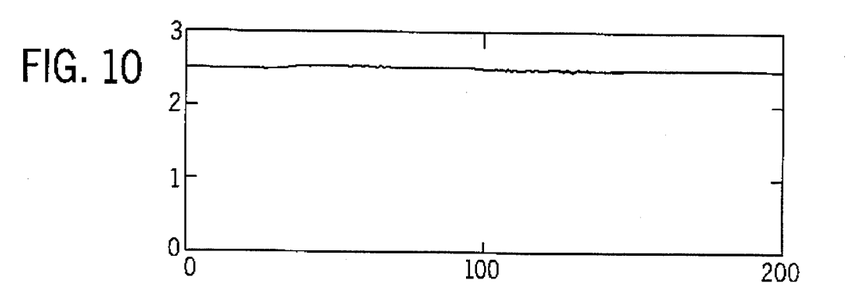
FIG. 10 is a representation of thermopile detector output voltage with thermal drift compensation according to the invention during the thermal response test illustrated in FIG. 7.

The corrected output signal V, which is the sum of the uncorrected detector output signal $V_{meas}(t)$ shown in FIG. 9 and the above-mentioned corrective compensation signal $V_{comp}(t)$, is plotted in FIG. 10. The corrected output signal V remains unchanged during the transient change of temperature. Time in the above formula is in seconds.

Instead of a thermocouple, the thermal radiation sensor may be a bolometer detector based on a resistive sensor/reference element pair.

We claim:

1. A method for compensating gas analyzer equipment for transient errors caused by temperature changes, said method comprising the steps of:

transmitting electromagnetic radiation through a sample containing a gas to be analyzed;

detecting the intensity of the radiation exiting the gas sample by means of a thermal detector having a radiation detecting sensor element and a reference sensor element, said thermal detector generating an output signal indicative of a property of the gas in the sample, changes in the temperature of the thermal detector introducing errors in the output signal;

obtaining a temperature measurement indicative of the temperature of the reference sensor element;

determining, from the temperature measurement, the rate of change of temperature of the reference sensor element as a function of time and providing a compensating signal indicative of same; and applying the compensating signal to the output signal of the thermal detector to provide a temperature compensated output signal indicative of the property of the gas in the sample.

2. A method as defined in claim 1 further defined as obtaining the temperature measurement by measuring the temperature of the reference sensor element.

3. A method as defined in claim 1 further defined as obtaining the temperature measurement by measuring the temperature at a location having, at least, temperature rate of change characteristics corresponding to those of the reference sensor element.

4. A method as defined in claim 3 wherein the thermal detector is housed in a case and wherein the temperature measurement is obtained from the case.

5. A method as defined in claim 3 wherein the gas analyzer equipment has a body structure containing the thermal detector and wherein the temperature measurement is obtained from the body structure.

6. A method as defined in claim 1 further defined as including the step of measuring the temperature of the gas to be analyzed and using same in the provision of the temperature compensated output signal.

7. A method as defined in claim 1 wherein the step of applying the compensating signal to the thermal detector output signal is further defined as adding the compensating signal to the thermal detector output signal.

8. The method as defined in claim 1 wherein the step of determining and providing the compensating signal is further defined as applying a proportionality coefficient to the rate of change of temperature of the reference sensor element.

9. The method as defined in claim 1 wherein the step of determining and providing the compensating signal is further defined as providing a compensating signal incorporating a time delay.

10. A method as defined in claim 1 wherein the step of determining and providing the compensating signal is further defined as providing a compensating signal that incorporates a polynomial function.

11. A method as defined in claim 10 wherein the step of determining and providing the compensating signal is further defined as providing a compensating signal that incorporates a polynomial function including a time delayed quantity.

12. A method as defined in claim 1 wherein the detection step is further defined as generating a thermal detector output signal indicative of the concentration of the gas in the sample.

13. Gas analysis apparatus in which compensation is provided for transient errors caused by temperature changes associated with said apparatus, said apparatus comprising:

a sample cell containing the gas to be analyzed;

an electromagnetic radiation source for passing electromagnetic radiation through the sample cell;

a thermal detector having a radiation detecting sensor element receiving the radiation exiting said sample cell, said thermal detector having a reference sensor element protected from said radiation, said thermal detector generating an output signal indicative of a property of the gas in the cell, changes in the temperature of the thermal detector introducing errors in the output signal;

temperature sensing means providing a temperature signal indicative of the temperature of the reference sensor element; and signal processing means coupled to said sensing means for determining the rate of change of temperature of said reference sensor element as a function of time and providing a compensating signal indicative of same, said signal processing means being coupled to said thermal detector and for altering the output signal of said thermal detector in accordance with the compensating signal to provide a temperature compensated output signal indicative of the property of the gas in said cell.

14. An apparatus as defined in claim 13 wherein said temperature sensing means is coupled in heat transfer relationship to said reference sensor element.

15. An apparatus according to claim 13 wherein said thermal detector has a case enclosing said radiation detecting sensor element and said reference sensor element and wherein said temperature sensing means in coupled in heat transfer relationship to said case.

16. An apparatus as defined in claim 13 further including a body structure in which said thermal detector is located, said body structure being formed to have low temperature rate of change characteristics when said apparatus is subjected to temperature changes.

17. An apparatus as defined in claim 16 wherein said body structure has temperature change characteristics resembling those of said reference sensing element and said temperature sensing means is coupled in heat transfer relationship to said body structure.

18. An apparatus as defined in claim 16 wherein said body structure includes a body piece surrounding said thermal detector, said body piece having high thermal conductivity characteristics.

19. An apparatus as defined in claim 18 wherein said body piece is enclosed in thermal insulation.

20. An apparatus as defined in claim 19 wherein said thermal insulation comprises expanded polyethylene plastic material at least two mm thick.

21. An apparatus as defined in claim 18 wherein said body piece comprises an aluminum block having a weight of approximately 170 grams.

22. An apparatus as defined in claim 18 wherein said body structure has a thermal time constant greater than 15 minutes for an abrupt change in ambient temperature of 10° K.

23. An apparatus as defined in claim 13 further including further temperature sensing means for measuring the temperature of the gas to be analyzed, said further temperature sensing means being coupled to said signal processing means.

24. An apparatus as defined in claim 23 wherein said temperature sensing means and said further temperature sensing means comprise a common temperature sensor.

25. An apparatus as defined in claim 13 wherein said signal processing means is further defined as adding the compensating signal to the output signal of the thermal detector.

26. An apparatus according to claim 13 wherein said signal processing means is further defined as providing a compensating signal in which a proportionality coefficient is applied to the rate of change of temperature of said reference sensor element with respect to time.

27. An apparatus according to claim 13 wherein said signal processing means is further defined as providing a compensating signal incorporating a time delay.

28. An apparatus according to claim 13 wherein said signal processing means is further defined as providing a compensating signal incorporating a polynomial function.

29. An apparatus according to claim 28 wherein said signal processing means is further defined as providing a compensating signal incorporating a polynomial function including a time delayed quantity.

30. An apparatus as defined in claim 13 wherein said thermal detector is further defined as generating an output signal indicative of the concentration of the gas in said sample cell.

* * * * *